(12) United States Patent
Hurlbert et al.

(10) Patent No.: US 9,283,088 B2
(45) Date of Patent: Mar. 15, 2016

(54) ARTIFICIAL INTERVERTEBRAL DISC

(75) Inventors: R. John Hurlbert, Calgary (CA);
Stephan J. Duplessis, Calgary (CA);
Lali Sekhon, Reno, NV (US)

(73) Assignee: Kinetic Spine Technologies, Inc., Calgary (CA)

(*) Notice: Subject to any disclaimer, the term of this patent is extended or adjusted under 35 U.S.C. 154(b) by 434 days.

(21) Appl. No.: 12/663,735

(22) PCT Filed: Jun. 12, 2008

(86) PCT No.: PCT/CA2008/001114
§ 371 (c)(1),
(2), (4) Date: Dec. 9, 2009

(87) PCT Pub. No.: WO2008/151426
PCT Pub. Date: Dec. 18, 2008

(65) Prior Publication Data
US 2010/0222885 A1 Sep. 2, 2010

Related U.S. Application Data

(60) Provisional application No. 60/934,277, filed on Jun. 12, 2007.

(51) Int. Cl.
*A61F 2/44* (2006.01)
*A61B 17/32* (2006.01)
*A61F 2/30* (2006.01)

(52) U.S. Cl.
CPC .............. *A61F 2/4425* (2013.01); *A61B 17/32* (2013.01); *A61F 2/30771* (2013.01); *A61F 2/44* (2013.01); *A61F 2002/30125* (2013.01); *A61F 2002/30131* (2013.01); *A61F 2002/30187* (2013.01); *A61F 2002/30563* (2013.01);
(Continued)

(58) Field of Classification Search
CPC ............ A61F 2/4425; A61F 2002/443; A61F 2002/30563; A61F 2002/30662; A61F 2002/30649; A61F 2/442; A61F 2002/30565
USPC .................. 623/17.11, 17.13–17.16
See application file for complete search history.

(56) References Cited

U.S. PATENT DOCUMENTS 4,759,769 A 7/1988 Hedman et al.
5,370,697 A * 12/1994 Baumgartner ........ A61F 2/4637
623/17.15

(Continued)

FOREIGN PATENT DOCUMENTS

CA 2514904 7/2005
WO 0247586 6/2002

(Continued)

*Primary Examiner* — Pedro Philogene
*Assistant Examiner* — Lynnsy Summitt
(74) *Attorney, Agent, or Firm* — Simpson & Simpson, PLLC

(57) ABSTRACT

An artificial intervertebral disc for implantation between two adjacent vertebrae includes superior and inferior shells connected in a ball and socket arrangement. The inferior shell preferably incorporating a convex portion that cooperates with a concave portion on the superior shell. A resilient nucleus is provided within an enclosure defined by the opposing inner surfaces of the shells and biases the shells against each other. The ball portion can be provided in either fixed or slidable arrangement. The artificial disc of the invention includes various resistance means for restricting and limiting the range of rotational and translational motion between the shells.

7 Claims, 10 Drawing Sheets

(52) U.S. Cl.
  CPC  *A61F 2002/30662* (2013.01); *A61F 2002/443* (2013.01); *A61F 2230/0008* (2013.01); *A61F 2230/0013* (2013.01); *A61F 2230/0034* (2013.01)

(56) References Cited

U.S. PATENT DOCUMENTS

| | | | |
|---|---|---|---|
| 5,562,738 A | 10/1996 | Boyd et al. | |
| 5,782,832 A | 7/1998 | Larsen et al. | |
| 6,063,121 A | 5/2000 | Xavier et al. | |
| 6,146,412 A | 11/2000 | Van Duren | |
| 6,146,421 A | 11/2000 | Gordon et al. | |
| 6,179,874 B1 | 1/2001 | Cauthen | |
| 6,572,653 B1 | 6/2003 | Simonson | |
| 6,679,915 B1 | 1/2004 | Cauthen | |
| 6,770,095 B2 | 8/2004 | Grinberg et al. | |
| 7,101,399 B2 | 9/2006 | Errico et al. | |
| 7,156,876 B2 | 1/2007 | Moumene et al. | |
| 7,195,644 B2* | 3/2007 | Diaz | A61F 2/4611 623/17.13 |
| 7,235,102 B2* | 6/2007 | Ferree | A61F 2/34 623/17.12 |
| 7,267,688 B2* | 9/2007 | Ferree | A61F 2/4425 623/17.11 |
| 7,641,692 B2 | 1/2010 | Bryan et al. | |
| 7,704,280 B2* | 4/2010 | Lechmann | A61F 2/4425 606/246 |
| 7,806,933 B2* | 10/2010 | Sears | A61F 2/4425 623/17.11 |
| 7,927,374 B2* | 4/2011 | Duggal | A61B 17/1604 623/17.14 |
| 2003/0135277 A1 | 7/2003 | Bryan et al. | |
| 2003/0204261 A1 | 10/2003 | Eisermann et al. | |
| 2003/0220691 A1* | 11/2003 | Songer | A61F 2/442 623/17.14 |
| 2003/0233146 A1* | 12/2003 | Grinberg | A61F 2/4425 623/17.14 |
| 2004/0024461 A1* | 2/2004 | Ferree | A61F 2/34 623/17.13 |
| 2004/0030387 A1 | 2/2004 | Landry et al. | |
| 2004/0030398 A1 | 2/2004 | Ferree | |
| 2004/0073310 A1* | 4/2004 | Moumene | A61F 2/442 623/17.13 |
| 2004/0093082 A1* | 5/2004 | Ferree | A61F 2/4425 623/17.11 |
| 2004/0093087 A1 | 5/2004 | Ferree et al. | |
| 2004/0193273 A1* | 9/2004 | Huang | A61F 2/442 623/17.12 |
| 2004/0225364 A1* | 11/2004 | Richelsoph | A61F 2/4425 623/17.13 |
| 2004/0243238 A1 | 12/2004 | Arnin et al. | |
| 2005/0015152 A1 | 1/2005 | Sweeney | |
| 2005/0038515 A1 | 2/2005 | Kunzler | |
| 2005/0049189 A1 | 3/2005 | Uchida et al. | |
| 2005/0085909 A1 | 4/2005 | Eisermann | |
| 2005/0149189 A1 | 7/2005 | Mokhtar et al. | |
| 2005/0149196 A1 | 7/2005 | Zucherman et al. | |
| 2005/0165485 A1 | 7/2005 | Trieu | |
| 2005/0171605 A1 | 8/2005 | Link et al. | |
| 2005/0203626 A1* | 9/2005 | Sears | A61F 2/4425 623/17.11 |
| 2006/0025862 A1* | 2/2006 | Villiers | A61F 2/4425 623/17.14 |
| 2006/0122703 A1 | 6/2006 | Aebi et al. | |
| 2006/0190084 A1 | 8/2006 | Doubler et al. | |
| 2006/0235526 A1 | 10/2006 | Lemaire | |
| 2007/0088441 A1* | 4/2007 | Duggal | A61B 17/1604 623/17.16 |
| 2008/0058944 A1 | 3/2008 | Duplessis et al. | |
| 2008/0065216 A1 | 3/2008 | Hurlbert et al. | |
| 2008/0161932 A1* | 7/2008 | Armstrong | A61F 2/4425 623/17.16 |
| 2009/0082867 A1* | 3/2009 | Sebastian Bueno | A61F 2/4425 623/17.16 |
| 2010/0010634 A1* | 1/2010 | Binotto | A61F 2/4425 623/17.16 |
| 2010/0298939 A1 | 11/2010 | Delfosse et al. | |

FOREIGN PATENT DOCUMENTS

| | | |
|---|---|---|
| WO | WO 2006116850 | 11/2006 |
| WO | WO 2006116852 | 11/2006 |

* cited by examiner

ARTIFICIAL INTERVERTEBRAL DISC

CROSS-REFERENCE TO RELATED APPLICATIONS

The present application is the U.S. national stage application pursuant to 35 U.S.C. §371 of International Application No. PCT/CA2008/001114, filed Jun. 12, 2008 which application claims priority to U.S. Provisional Patent Application No. 60/934,277 filed on Jun. 12, 2007, which applications are incorporated herein by reference in their entireties.

FIELD OF THE INVENTION

The present invention relates to the field of spinal implants and, more particularly, to intervertebral disc replacements that provide dynamic spinal stabilisation.

DESCRIPTION OF THE PRIOR ART

The spine is a complicated structure comprised of various anatomical components, which, while being extremely flexible, provides structure and stability for the body. The spine is made up of vertebrae, each having a ventral body of a generally cylindrical shape. Opposed surfaces of adjacent vertebral bodies are connected together and separated by intervertebral discs (or "discs"), comprised of a fibrocartilaginous material. The vertebral bodies are also connected to each other by a complex arrangement of ligaments acting together to limit excessive movement and to provide stability. A stable spine is important for preventing incapacitating pain, progressive deformity and neurological compromise.

The anatomy of the spine allows motion (translation and rotation in a positive and negative direction) to take place without much resistance but as the range of motion reaches the physiological limits, the resistance to motion gradually increases to bring the motion to a gradual and controlled stop.

Intervertebral discs are highly functional and complex structures. They contain a hydrophilic protein substance that is able to attract water thereby increasing its volume. The protein, also called the nucleus pulposis, is surrounded and contained by a ligamentous structure called the annulus fibrosis. The main function of the discs is load bearing (including load distribution and shock absorption) and motion. Through their weight bearing function, the discs transmit loads from one vertebral body to the next while providing a cushion between adjacent bodies. The discs allow movement to occur between adjacent vertebral bodies but within a limited range thereby giving the spine structure and stiffness.

Due to a number of factors such as age, injury, disease etc., it is often found that intervertebral discs lose their dimensional stability and collapse, shrink, become displaced, or otherwise damaged. It is common for diseased or damaged discs to be replaced with prostheses and various versions of such prostheses, or implants, as are known in the art. One of the known methods involves replacement of a damaged disc with a spacer into the space occupied by the disc. However, such spacers also fuse together the adjacent vertebrae thereby preventing any relative movement there-between.

More recently, disc replacement implants that allow movement between adjacent vertebrae have been proposed. Examples of some prior art implants are provided in the following US patents: U.S. Pat. No. 5,562,738 (Boyd et al.); U.S. Pat. No. 6,179,874 (Cauthen); and U.S. Pat. No. 6,572,653 (Simonson).

Unfortunately, the disc replacement (i.e. implant) solutions taught in the prior art are generally deficient in that they do not take into consideration the unique and physiological function of the spine. For example, many of the known artificial disc implants are unconstrained with respect to the normal physiological range of motion of the spine in the majority of motion planes. Although some of the prior art devices provide a restricted range of motion, such restrictions are often outside of the normal physiological range of motion; thereby rendering such devices functionally unconstrained. Further, the known unconstrained implants rely on the normal, and in many cases diseased structures such as degenerated facets, to limit excessive motion. This often leads to early or further facet joint degeneration and other collateral damage to spinal components.

In addition, many of the artificial discs known in the art do not provide mechanisms for minimising stress upon adjacent structures caused by sudden motions.

One intervertebral disc that addresses many of the aforementioned deficiencies in the prior art is provided in PCT application publication no. WO 2006/116852, which shares the same inventors as the present invention and the entire contents of which are incorporated herein by reference. Nevertheless, there exists a need for a further intervertebral disc prosthesis that provides similar advantages.

SUMMARY OF THE INVENTION

In one aspect, the present invention provides an implant for replacing intervertebral discs.

In another aspect, the invention provides an artificial intervertebral disc that allows adjacent vertebrae a range of motions in various planes. Such motion may be limited to a predetermined range, within which movement of adjacent vertebrae does not lead to deterioration of neighbouring spinal structural components.

In another aspect, the above-mentioned motion about various axes can be coupled to more closely simulate natural movement.

In another embodiment, the invention provides an artificial disc that enables specific adjustment of the instantaneous axis of rotation between the adjacent vertebrae.

In another embodiment, the invention provides an artificial disc that enables dynamic variability of the instantaneous axis of rotation.

Thus, in one aspect, the invention provides an artificial intervertebral disc for implantation between adjacent superior and inferior vertebrae of a spine, the disc comprising:
a superior shell, an inferior shell, and a resilient nucleus;
the inferior shell having a superior surface comprising a posteriorly positioned convex portion and a well;
the superior shell having an inferior surface opposing the superior surface of the inferior shell, and comprising a posteriorly positioned concave portion, opposite the convex portion, and a recess, opposite the first well;
the well and recess combining to form an enclosure to contain the nucleus;
the convex and concave portions being in articulating cooperation to form a ball and socket joint.

In further embodiment, the invention provides an artificial intervertebral disc for implantation between adjacent superior and inferior vertebrae of a spine, the disc comprising:
a superior shell, an inferior shell, and a resilient nucleus;
the inferior shell having a superior surface comprising a posteriorly positioned convex portion and a well;
the superior shell having an inferior surface opposing the superior surface of the inferior shell, and comprising a posteriorly positioned concave portion, opposite the convex portion, and a recess, opposite the first well;

the well and recess combining to form an enclosure to contain the nucleus;

the convex and concave portions being in articulating cooperation to form a ball and socket joint;

and wherein the convex portion is slidably contained within a housing in the inferior shell.

BRIEF DESCRIPTION OF THE DRAWINGS

The features of the invention will become more apparent in the following detailed description in which reference is made to the appended drawings wherein.

DETAILED DESCRIPTION OF THE INVENTION

In the following description, the terms "superior", "inferior", "anterior", "posterior" and "lateral" will be used. These terms are meant to describe the orientation of the implants of the invention when positioned in the spine. Thus, "superior" refers to a top portion and "posterior" refers to that portion of the implant (or other spinal components) facing the rear of the patient's body when the spine is in the upright position. Similarly, the term "inferior" will be used to refer to the bottom portions of the implant while "anterior" will be used to refer to those portions that face the front of the patient's body when the spine is in the upright position. With respect to views shown in the accompanying figures, the term "coronal" will be understood to indicate a plane extending between lateral ends thereby separating the body into anterior and posterior portions. The term "sagittal" will be understood to indicate a plane extending anteroposterior thereby separating the body into lateral portions. The term "axial" will be understood to indicate a plane separating the body into superior and inferior portions. It will be appreciated that these positional and orientation terms are not intended to limit the invention to any particular orientation but are used to facilitate the following description.

The present invention provides artificial discs or implants for replacing intervertebral discs that are damaged or otherwise dysfunctional. The implants of the present invention are designed to allow various degrees of motion between adjacent vertebral bodies, but within acceptable limits.

Figure 1:
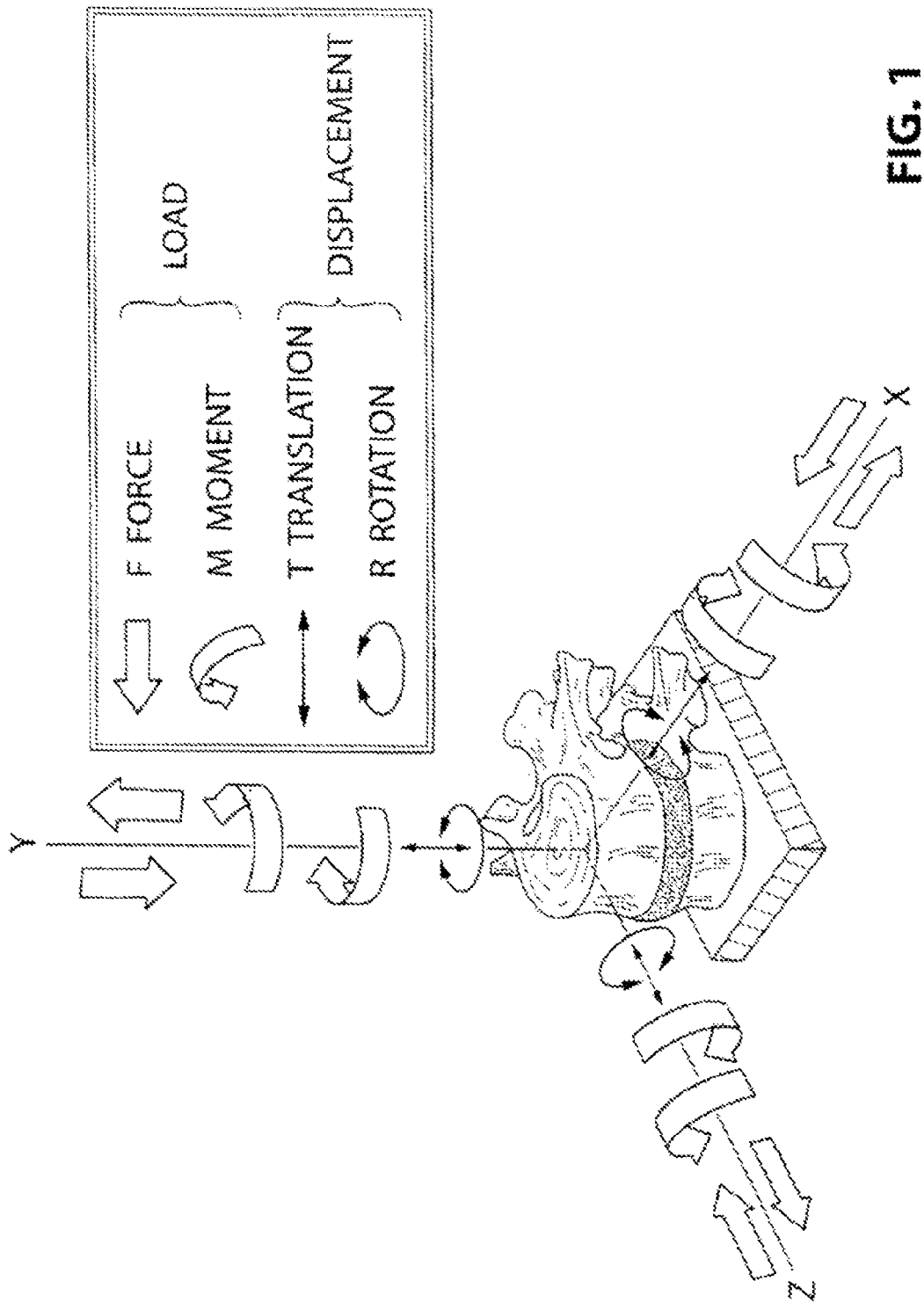
FIG. 1 is a schematic illustration of the range of motion of a vertebra.

FIG. 1 illustrates the complexity of vertebral movement by indicating the various degrees of freedom associated therewith. In the normal range of physiological motion, vertebrae extend between a "neutral zone" and an "elastic zone". The neutral zone is a zone within the total range of motion where ligaments supporting the spinal bony structures are relatively non-stressed; that is, the ligaments offer relatively little resistance to movement. The elastic zone is encountered when the movement occurs at or near the limit of the range of motion. At this zone, the visco-elastic nature of the ligaments begins to provide resistance to the motion thereby limiting same. The majority of "everyday" or typical movements occurs within the neutral zone and only occasionally continues into the elastic zone. Motion contained within the neutral zone does not stress soft tissue structures whereas motion into the elastic zone will cause various degrees of elastic responses. Therefore, a goal in the field of spinal prosthetic implants in particular, is to provide a prosthesis that restricts motion of the vertebrae adjacent thereto to the neutral zone. Such restriction minimises stresses to adjacent osseous and soft tissue structures. For example, such limitation of movement will help to minimize or otherwise reduce facet joint degeneration.

In general terms, the present invention provides an implantable spinal prosthesis for replacing intervertebral discs. The implant of the invention is generally comprised of cooperating inferior and superior portions, or shells, that are movable relative to each other and being separated along at least a portion thereof by a resilient, force absorbing nucleus. The relative movement between the components of the disc of the invention includes various degrees of freedom but is generally limited to a specified range. That is, the prosthesis is provided with various "soft" and "hard" stops to limit motion between the vertebrae adjacent thereto. In particular, the artificial disc of the invention provides for rotation, flexion, extension and lateral motions that are similar to normal movements in the neutral and elastic zones (i.e. the movements associated with a normal or intact disc). In addition, the device of the invention also allows various combinations of such motions, or coupled motions. For example, the disc of the invention can be subjected to flexion and translation, or lateral flexion and lateral translation, or flexion and rotation. Various other motions will be apparent to persons skilled in the art given the present disclosure.

Figure 2:
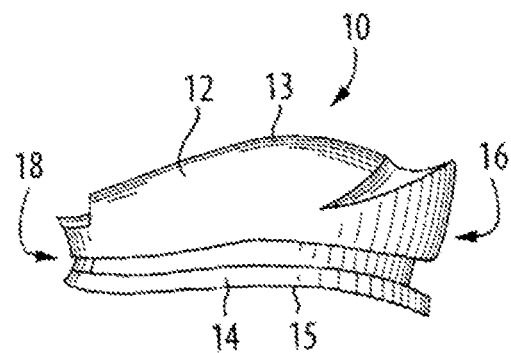
FIG. 2 is a side elevation of an artificial intervertebral disc according to one embodiment of invention.
Figure 3:
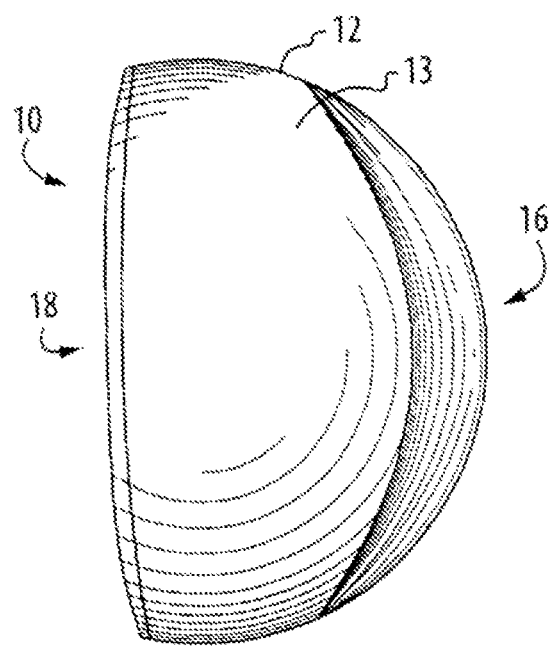
FIG. 3 is a top view of the disc of FIG. 2.

FIGS. 2 and 3 illustrate an artificial intervertebral disc 10 according to an embodiment of the invention. As shown, the disc 10 includes a superior shell 12 and an inferior shell 14 and comprises anterior 16 and posterior 18 ends. The outer superior and inferior surfaces, 13 and 15 respectively, of the shells 12 and 14 may be provided with desired surface structures or shapes as may be needed for enhancing or facilitating implantation in the space between the neighbouring vertebral body structures. For example, in the embodiment shown, the superior outer surface 13 of the superior shell may be convexly shaped. In addition, the surfaces 13 and 15 may be provided with any known coating or surface treatment to facilitate and/or cause bony in-growth and/or to otherwise promote adhesion to the adjacent bone structures. Such coatings etc. will be known to persons skilled in the art. In addition, the outer surfaces of the shells 12 and 14 may be provided with further anchoring devices for securing the disc 10 to the adjacent bone structures. Such devices may include, for example, screws, spikes, holes or pins (not shown) for facilitating or enhancing implantation of the invention between adjacent vertebral bodies.

In addition, the disc 10 of the invention can be adapted for use in association with artificial vertebral bodies. In such case, the disc 10 of the invention may be provided with various anchoring means such as keels and the like (not shown) that can be used for securing to artificial vertebral bodies. An example of such an artificial body is provided the present applicant's co-pending PCT application published under number WO 2006/116850, the entire contents of which are incorporated herein by reference. In general, the disc 10 of the invention may be provided with any external surface or surface means that would facilitate attachment to an adjacent surface of an artificial vertebral body when the two structures are in combination. The attachment means may allow some degree of relative movement between the artificial disc and artificial vertebral body. Thus, although in one embodiment (as shown in FIGS. 2 and 3), the outer inferior surface 15 is provided with a curved geometry to adapt to a naturally occurring vertebral body, it may equally be provided with a different structure that is adapted to engage or cooperate with a surface of an artificial vertebral body. Both the artificial disc and the artificial body may be designed so as to allow such cooperative arrangement there-between.

Figure 5:
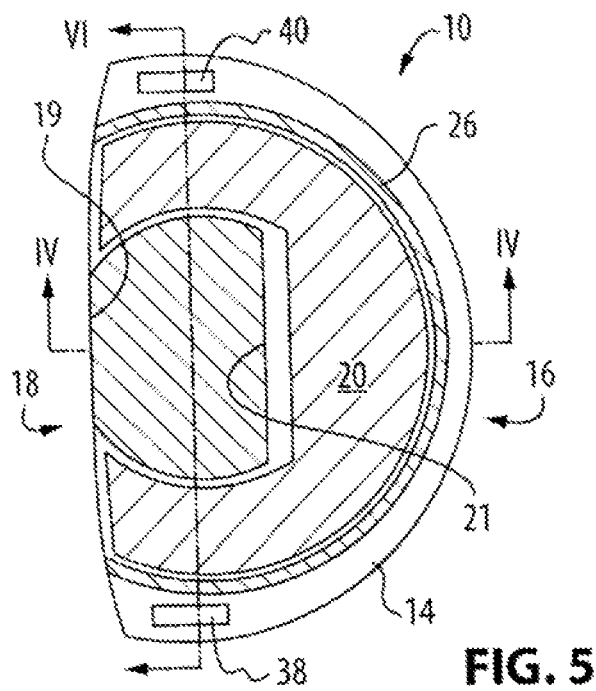
FIG. 5 is top or superior cross sectional view of the inferior shell of the disc of FIG. 2 taken along the axial plane V-V shown in FIG. 6.

As shown in FIGS. 3 and 5, the disc 10 of the invention is preferably provided with a generally oblong, oval or elliptical configuration when viewed from the top (superiorly) or bottom (inferiorly). This shape of the disc will be understood by persons skilled in the art to be preferred in terms of maximising surface contact with the adjacent vertebral bodies. However, various other shapes, sizes and proportions will be possible. As also shown, the disc 10 may preferably be provided with a specific external shape that may be different superiorly and inferiorly. For example, the external aesthetic characteristics illustrated in the figures attached hereto may facilitate implantation in existing bone structures by reflecting the natural shape of the adjacent vertebral structures. However, it will be appreciated that the invention is not limited to any shape or size. In addition, it will be appreciated that the external shape of the disc illustrated in the accompanying figures may not be needed or suitable for use with artificial vertebral bodies.

Figure 4:
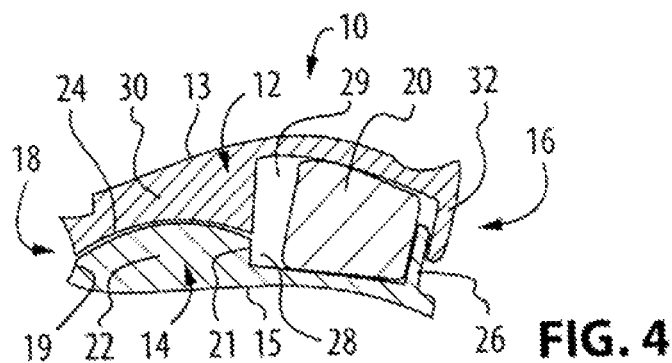
FIG. 4 is a side or lateral cross sectional elevation of the disc of FIG. 2 taken along the sagittal plane IV-IV shown in FIG. 5.
Figure 6:
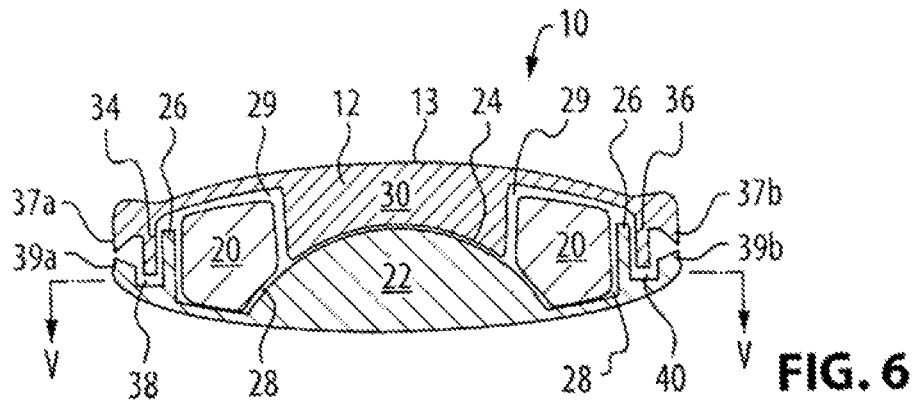
FIG. 6 is a front or anterior cross sectional view of the disc of FIG. 2 taken along the coronal plane VI-VI shown in FIG. 5.

The disc 10 is shown in sagittal cross section in FIG. 4. As shown, the inferior and superior shells 12 and 14 are arranged in a cooperative manner to form the disc 10. Between the shells 12 and 14 is provided a resilient nucleus 20. As shown in FIGS. 4 to 6, the inner (or superior) surface of the inferior shell 14 includes a raised convex portion 22 proximal to the posterior end 18. The convex portion 22 cooperates with a concave portion or surface 24 provided on the inner (or inferior) surface of the superior shell 12 to form a ball and socket type of joint, as discussed further below. As will be understood, such a joint allows for the shells 12 and 14 to be in articulating cooperation thereby allowing relative movement in various directions. As shown in FIGS. 4 and 5, in one embodiment, the convex portion or ball 22 may be located at the posterior end 18 of the inferior shell. The posterior and anterior ends, 19 and 21, of the ball 22 are preferably truncated or squared off. As will be understood by persons skilled in the art and as described further below, the shape, position and dimensions of the convex portion 22 and/or concave portion 24 can be adjusted depending upon the desired range or extent of motion, or axis of rotation.

The inferior shell also includes an upward extending outer wall 26 thereby resulting in a well, 28 bounded between the convex portion or ball 22 and the outer wall 26, within which is contained the nucleus 20. As shown in FIG. 5, the well 28 of the illustrated embodiment generally has a "U" shaped structure with the arms of such "U" extending posteriorly. The nucleus 20 is preferably provided with a similar structure so the nucleus conforms to the shape of the well 28 and is accommodated therein. However, as will be understood and as discussed further below, the well 28 and/or the nucleus 20 may be provided with other shapes to achieve the same function.

As illustrated in FIGS. 4 and 6, the superior shell 12 is provided with a downward extending posterior portion 30 the inferior surface of which comprises the aforementioned concave surface 24 or socket. As discussed above, the concave surface or socket 24 of the superior shell 12 is adapted or designed to cooperate with the convex portion or ball 22 of the inferior shell so as to form an articulating joint there-between. The superior shell 12 also includes a downward extending rim 32 at least along the anterior end thereof. The rim 32 is sized to lie in front of, or anteriorly of, the wall 26 of the inferior shell. As will be discussed further below, this arrangement serves to provide a "hard stop" for flexion and extension movements, that is a movement wherein the superior shell is moved anteriorly or posteriorly over the inferior shell. The disc shown in FIG. 4 illustrates the superior shell 12 in a position where the rim 32 thereof contacts the wall 26 of the inferior shell thereby preventing any further posterior movement of the superior shell 12. It will be understood that the rim 32 and wall 26 of the shells do not need to be continuous or extend along the entire periphery of the respective shells.

As shown in FIGS. 4 and 6, the superior shell includes a recess 29 surrounding the posterior socket portion 24. The recess 29 is generally the same shape as the well 28 of the inferior section whereby the recess and well 28 combine to form an enclosure for the nucleus.

As shown in FIG. 6, the superior shell 12 may preferably also be provided with a pair of downward extending tabs 34, 36 on the lateral ends thereof. The tabs 34 and 36 are adapted to be received within slots 38 and 40, respectively, the slots being provided on the lateral ends of the inferior shell 14. As taught for example in the present applicant's co-pending PCT application published under number WO 2006/116852, this type tab and slot arrangement serves to provide a "hard stop" for lateral bending motions as well as axial rotation motions.

More specifically, in the case of lateral motions, as can be seen in FIG. 6, the slots 38 and 40 extend deeper into the inferior shell 14 than the length of the tabs 34 and 36. Thus, a lateral or side to side movement between the superior and inferior shells will cause the terminal end of one of the tabs to contact the base of the respective slot thereby preventing any further movement in that direction. In the case of axial rotation, the slots 38 and 40 will be sized to be wider than the tabs 34 and 36, thereby allowing the superior and inferior shells to be rotated over the ball 22 and socket 24 joint formed there-between until the side edges of the tabs 34 and 36 contact the side walls of the table 38 and 40. Further details concerning such tabs and slots are provided in applicant's aforementioned co-pending application. It will understood that the ovoid shape of the disc itself may also provide any necessary "stop" for rotation motion, thereby avoiding the need for the tabs (34, 36) and slots (38, 40). It will also be understood that the disc 10 may be unconstrained with respect to rotational movement or, alternatively, may be designed to inhibit any rotational movement. The degree of permissible rotation of the disc will depend on various factors as will be known to persons skilled in the art.

As shown in FIGS. 4 and 6, the resilient nucleus 20 serves to provide resistance to relative movement of the inferior and superior shells 12 and 14. For example, as shown in FIG. 4, the nucleus 20 resiliently biases the anterior ends of the shells 12 and 14 apart from each other wherein, due to the resilient nature of the nucleus, a compressive force applied to the anterior portion of the disc causes the anterior portions of the shells to be brought closer together. This type of motion of the shells would occur, for example, during a flexion movement (i.e. where the superior shell 12 is moved anteriorly with respect to the inferior shell 14).

FIG. 6 illustrates an optional structure wherein outer angled edges are provided on the superior and inferior shells 12 and 14, primarily at the respective lateral ends thereof. As shown, the superior shell 12 includes downwardly angled edges 37a and 37b on the opposite lateral ends while the inferior shell 14 includes upwardly angled edges 39a and 39b. The edges 37a and 37b are arranged in opposing manner to the edges 39a and 39b, respectively. As illustrated, the arrangement of the edges 37a,b and 39a,b would result in a pincer-like function when the disc 10 is compressed laterally (i.e. along the coronal plane). This arrangement serves to shear any scar tissue that may form around the disc 10 once implanted and subjected to normal movements.

Figures 7, 8:
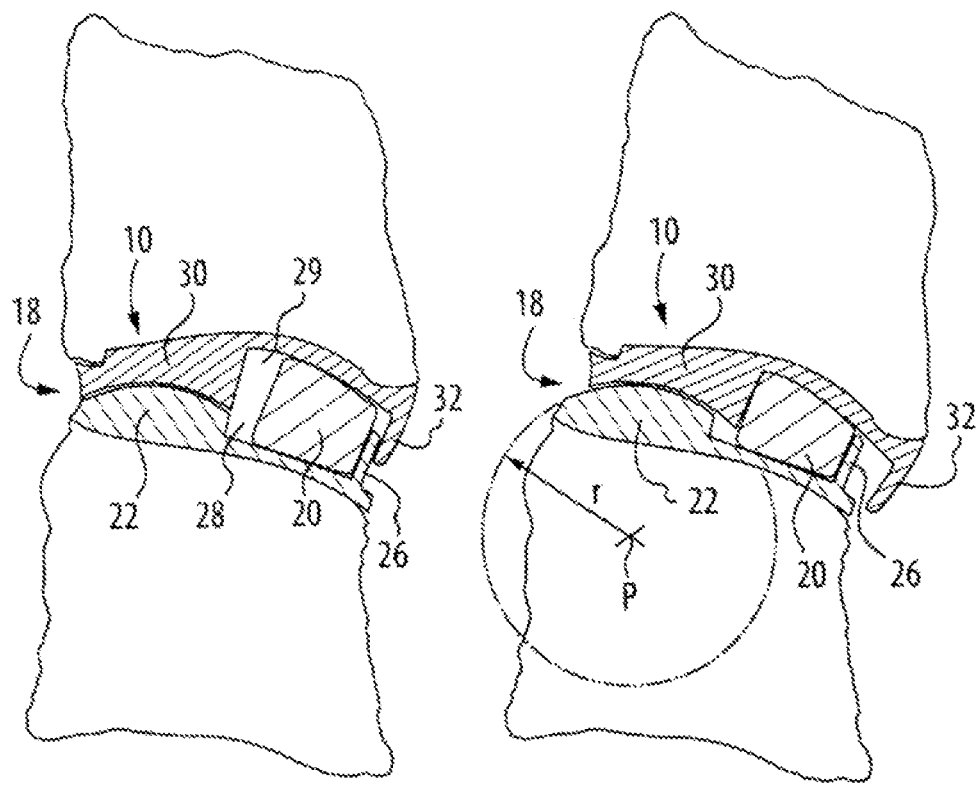
FIGS. 7 and 8 are cross sectional elevations of the disc of FIG. 2 implanted in a spine and illustrating the disc in extension and flexion positions, respectively.

FIGS. 7 and 8 illustrate a flexion movement of the invention. As shown, the disc 10 is illustrated in its implanted state within the intervertebral space created after excision of a damaged or diseased intervertebral disc. The disc 10 is shown in an extended position in FIG. 7 and in a flexion position in FIG. 8. As can be seen, in the extended position, FIG. 7, the superior and inferior shells 12 and 14 are in the position shown earlier in FIG. 4 and the nucleus 20 is contained within the enclosure formed by the well 28 and recess 29. However, as the superior vertebra is moved anteriorly in a flexion motion, the socket 30 of the superior shell 12 is slidably moved over the ball 22 of the inferior shell 14. As shown in FIG. 8, in the course of such flexion motion, the anterior wall of the socket portion 30 impinges against the resilient nucleus 20, which in turn is forced against the wall 26 of the inferior shell 14. As also shown, in the course of the flexion motion, the volume of the enclosure 29 containing the nucleus 20 is reduced as a result of the socket 30 of the superior shell 12 sliding over the ball 22 of the inferior shell. As illustrated, in this manner, the anterior end of the superior shell is vertically lowered thereby constricting the volume of the enclosure 29. As will be understood, such flexion movement can be continued until the nucleus is no longer compressible within the enclosure, at which point further flexion is prevented. Such compression of the nucleus would be understood to serve as a "soft" stop for the respective motion between the shells.

In one possible embodiment of the invention, the disc 10 may also utilize the tabs 34, 36 and slots 38, 40 described above as a "hard stop" for flexion movements. That is, in order to limit flexion, the tabs and slots may be sized to permit only a certain degree of movement until the anterior edges of the tabs 34, 36 contact the anterior walls of the slots 38, 40, at which point, further flexion is prevented.

In the flexion movement discussed above, the contact surface between the nucleus 20 and the inner walls of the recess 29 may be subjected to frictional forces. As such, the invention provides for the walls of the recess 29 to be provided with any known coating or treatment etc. to minimise such frictional forces thereby preventing damage to the nucleus 20.

FIG. 8 also illustrates the curvature of the ball or convex portion 22. As shown, the ball 22, preferably comprises a spherical surface having a radius "r" originating from a point P within the inferior vertebra. As illustrated, the point "P", which defines the instantaneous axis of rotation for the disc 10, is situated in the posterior portion of the inferior vertebra. This positioning is a result of the posteriorly positioned point or articulation formed by the ball 22 and socket 24.

In certain cases, the implantation of an artificial disc may also require realignment of the adjacent vertebrae to alleviate a specific pathology. For example, the vertebrae may need to be realigned to restore lordosis. As will be understood, the present invention allows for the instantaneous axis of rotation of the disc to be positioned at various desired locations depending upon the need. The repositioning of the axis of rotation can be accomplished, for example, by changing the geometry and location of the ball 22 provided in the disc 10 of the invention. That is, by changing the shape of the ball 22 the instantaneous axis of rotation can be moved anteriorly or posteriorly. Thus, in the illustration of FIG. 8 for example, the point P can be moved in the anterior or posterior directions by adjusting the position of the ball 22 and the associated socket 24. In addition, it can also be understood that the curvature of the ball 22 may also be adjusted either together or independent of the location thereby also permitting the vertical positioning of the point P to be varied. For example, by reducing the radius "r" discussed above, it will be understood that the instantaneous axis of rotation (i.e. point "P" illustrated in FIG. 8) can be vertically raised so as to lie closer to the inferior shell 14 of the disc 10. In such position, the shear stresses applied to the facet joints between the adjacent vertebrae can be reduced.

In a further embodiment, the curvature of the convex portion 22 may be of various non-spherical shapes. For example, by adjusting the curvature to be more pronounced at the anterior end, the convex portion 22 may be adapted to act as a motion inhibitor to flexion. It will be understood that such adjustments to the convex portion or ball 22 can be made for one or more motions while still maintaining the desired ball and socket arrangement.

As indicated above, the resilient nucleus 20 provides an increasing resistance to flexion. Since such resistance is dependent upon the compressibility of the material comprising the nucleus, it will be understood that the degree of flexion can be tailored by choosing the appropriate characteristics of such material. For example, a nucleus made of a less compressible material or a nucleus that occupies more volume of the enclosure in which it is contained will have a reduced range of motion. As described above, the nucleus 20 is preferably provided with a generally "U" shaped structure so the nucleus more readily conforms to the shape of the generally "U" shaped well 28. However, as will be understood, the well 28 and/or the nucleus 20 may be provided with other shapes to achieve the same function. For example, in one embodiment, the nucleus 20 may be contained solely in the anterior section of the well and not within the arms of the 'U' shape. For example, the nucleus may have an elongate (i.e. oval, ovoid or oblong) structure. In such case, it will be understood that the well 28 or the enclosure 29 may be provided with a wall or other such barrier means to prevent displacement of the nucleus. In another embodiment, the nucleus may comprise a generally round structure that is located only at the anterior portion of the disc. In such case, it will be understood that the "soft" stop offered by the nucleus may only be effective in flexion movements. In the above description, the nucleus has been referred to as a singular body. However, in other embodiments, the nucleus may be provided in one or several pieces since the resilient nature of the nucleus would enable it to assume the shape of the well (or specific section of the well) once the superior shell has been combined. For example, in one embodiment, the nucleus may be provided in three segments corresponding to an anterior segment and two lateral segments. In yet another embodiment, the nucleus may be provided in two segments, each of which is located in the lateral sections of the enclosure of the disc (such as within the two arms of the "U" shaped well). In such case, it will be understood that the nucleus may only be effective as a "soft" stop for lateral bending movements. If, however, the two nucleus segments are elongated towards the anterior section of the disc, it will be understood that at least some degree of a "soft stop" would be provided for flexion movement. In general, the nucleus of the invention preferably provides a "soft" stop for flexion and lateral compressive movements. Thus, on this basis and in view of the present disclosure, various other modifications of the shape and size of the nucleus and/or well will be apparent to persons skilled in the art.

Figure 19:
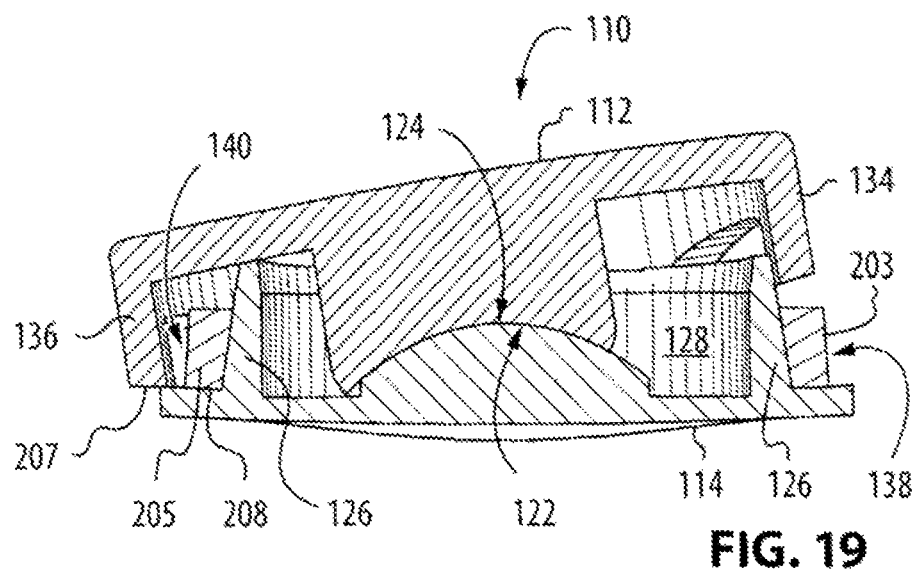
FIG. 19 is a rear cross sectional elevation of the disc of FIG. 12 in a laterally extended state.

Although the above discussion has focussed on flexion, it will be understood that the disc of the invention also allows for various other individual or coupled movements. For example, as mentioned above, the invention allows for controlled lateral movements of the vertebrae adjacent to the disc 10. In the embodiment illustrated in FIG. 6, a nucleus 20 having a generally "U" shaped structure includes arms of the "U" that are provided within lateral positions of the enclosure formed by the superior 12 and inferior 14 shells. That is, the arms of the generally "U" shaped nucleus occupy the lateral portions of the well 28. In this arrangement, it will be understood that during a lateral (i.e. side to side) movement, one of the lateral ends of the disc will be subjected to compression. This is also illustrated in FIG. 19. This movement will result in compression of the lateral section of the nucleus corresponding to the side that is under compression. As discussed above with respect to flexion and extension, the resilient nature of the nucleus would serve also to gradually limit the amount of lateral compression until a maximum amount of nucleus compression occurs. This therefore provides the "soft" stop for lateral movement. Such movement can be controlled as indicated above by selecting the appropriate choice of material for the nucleus and/or by the volume of nucleus contained within the enclosure of the disc. As discussed above, although a nucleus having the aforementioned "U" shaped structure may be preferred, the artificial disc of the invention may also be provided with a nucleus of any geometry. For example in the case where the nucleus comprises an oval, ovoid or otherwise oblong structure, it will be understood that at least some degree of lateral compression would still occur thereby allowing such nucleus to provide the above mentioned "soft" stop for lateral movements. Alternatively, the nucleus may be designed to provide a "soft" stop only for flexion and extension movements. Such options will be apparent to persons skilled in the art upon reviewing the present disclosure.

In another aspect, the various "hard stops" of the disc 10, as discussed above, can be tailored to provide more or less range of motion depending on the need of the patient and upon the natural motion requirements of the vertebrae in question.

Figure 9:
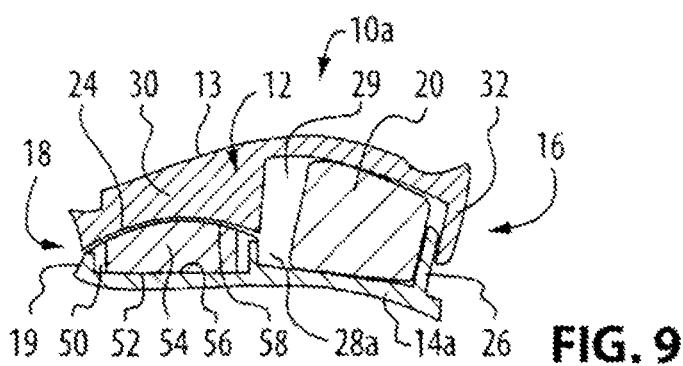
FIG. 9 is a side or lateral cross sectional elevation of the disc of the invention according to another embodiment taken along the sagittal plane IX-IX shown in FIG. 10.
Figure 10:
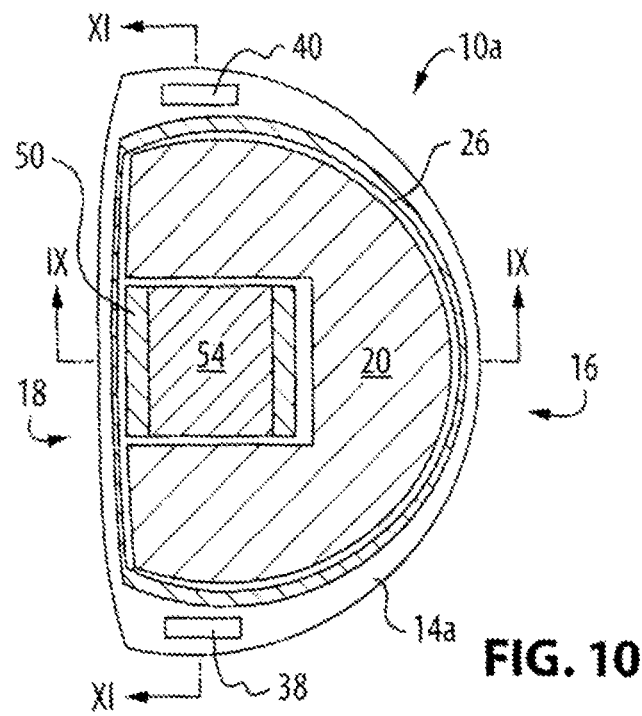
FIG. 10 is a top or superior cross sectional view of the inferior shell of the disc of FIG. 9 taken along the axial plane X-X shown in FIG. 11.
Figure 11:
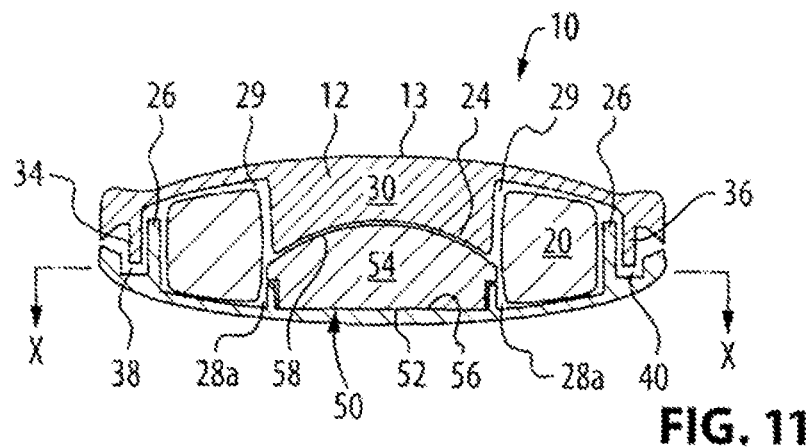
FIG. 11 is a front or anterior cross sectional elevation of the disc of FIG. 9 taken along the coronal plane XI-XI shown in FIG. 10.

Another embodiment of the invention is illustrated in FIGS. 9 to 11 wherein like elements are identified with the same reference numerals as above. Elements that are similar but include variations are identified with the same reference numeral but with the letter "a" added for clarity.

As shown in FIGS. 9 to 11, the general structure of the disc 10a is similar to that described above. In addition, the superior shell 12 comprises the same structure discussed above. However, the inferior shell 14 is modified to provide a means for dynamically varying the instantaneous axis of rotation. More specifically, in the embodiment shown, the fixed convex or ball portion 22 of the inferior shell 14a is replaced with a movable core 54 having a convex superior surface. As shown in FIGS. 9 to 11, the inferior shell 14a is provided with a recess 50, which, in one embodiment, is located at the posterior end 18 of the inferior shell 14 and generally centrally between the lateral ends thereof. However, based on the present disclosure, it will be understood that the recess 50 can be located at any position depending upon the need. The recess 50 includes a generally planar base 52 and is adapted to receive the movable, or floating core 54. The core 54 has a generally flat inferior surface 56 that is capable of sliding over the base 52 of the recess 50.

As shown in FIGS. 9 to 11, the core 54 comprises a convex superior surface 58 that is adapted to cooperate with the concave or socket portion 30 of the superior shell 12. Thus, the convex surface 58 serves the same function as the convex surface 22 discussed above. In a preferred embodiment, the convex superior surface, or ball, 58 of the core 54 has a spherical shape with an axis of rotation, such as point "P" discussed above, which, when implanted, lies within the inferiorly adjacent vertebral body. In addition, as with the embodiment discussed above, the geometry of the convex surface 58 of the core can be tailored to position the instantaneous axis of rotation (i.e. point "P", not shown) at any desired location. However, the embodiment of FIGS. 9 to 11 allows a further variability of the positioning of such rotational axis by providing a recess 50 that includes one or more dimensions that are larger than the core 54. For example, in one embodiment, the recess 50 may be larger than the core as measured in the sagittal plane thereby allowing the core 54 to slide anteroposteriorly, which, as will be understood, would translate the instantaneous axis of rotation in the course of normal movement of the patient. The degree of such sliding motion can be pre-determined by providing as little or as much clearance as needed between the core 54 and the recess 50.

In the embodiment illustrated in FIGS. 9 to 11, the size of the recess 50 across the coronal plane is very close to that of the core 54 thereby preventing any lateral shifting of the core while still allowing anterior-posterior movement. However, in another embodiment, the recess 50 of the inferior shell 14a may be sized to allow such lateral movement of the core as well. Thus, by sizing the recess 50 as needed the core 54 can be allowed a freedom of movement in sagittal and/or coronal planes.

The disc of the invention can be made with a variety of materials as will be known to persons skilled in the art. For example, the shells may be manufactured from metals (such as stainless steel, titanium, titanium alloys, nickel-titanium alloys, such as Nitinol™, cobalt-chrome alloys, etc.), porcelain, and plastic and/or thermoplastic polymers (such as PEEK™) or any combination thereof. In addition, it will be understood that the "ball" of the inferior shell and/or "socket" of the superior shell may be made from materials that are the same or different from the remainder of the respective shells. For example, the "ball" may be made of titanium while the "socket" and both shells are made of PEEK. Various other combinations of materials will be known to persons skilled in the art.

The nucleus 20 of the invention has been described generally as comprising a resilient material. In one embodiment, such material comprises a hydrogel, which is a material known in the art. However, alternative materials may also be used for the nucleus. For example, the nucleus may comprise mechanical springs (for example made of metal), hydraulic pistons, a hydrogel or silicone sac, rubber, a polymer or elastomer material, or any other such resilient material or device. One example of a suitable polymer material for the nucleus would be carbothane. Generally, the nucleus is made from resiliently compressible materials that serve to limit movement between the superior and inferior shells 12 and 14, 14a as described above and to provide a force for returning the disc 10, 10a to its neutral position.

Another embodiment of the invention is illustrated in FIGS. 12 to 21 wherein elements similar to those described above are identified with the prefix "1". As shown, the disc 110 according to the illustrated embodiment includes a superior shell 112 and an inferior shell 114. The outer surfaces of the artificial disc 110 may be provided with any shape or surface treatment as may be required. For example, as discussed above, the superior surface 113 of the superior shell 112 may be provided with a shape that conforms to the shape of the vertebral body that the disc 110 will contact when implanted.

Figure 12:
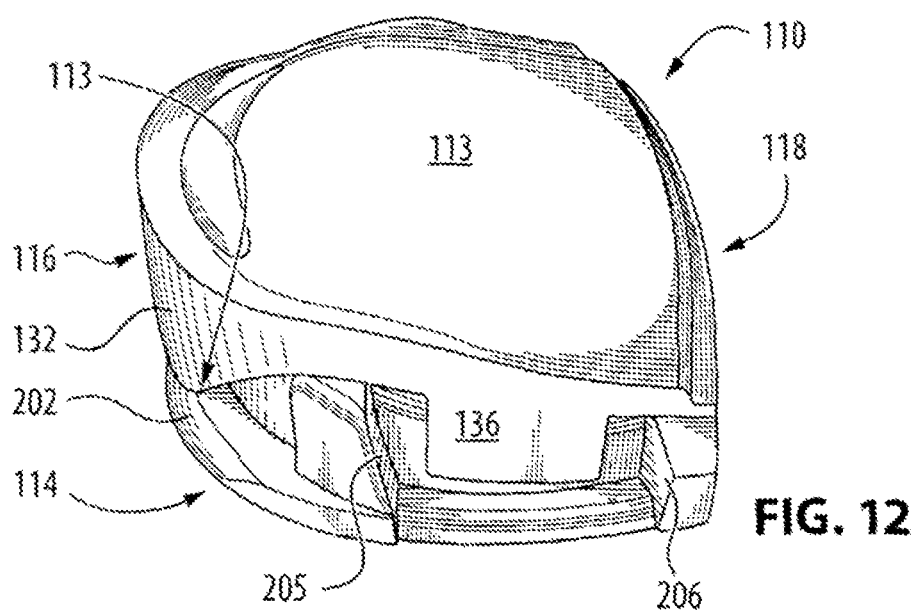
FIG. 12 is a side perspective elevation of the disc of the invention according to another embodiment.
Figure 13:
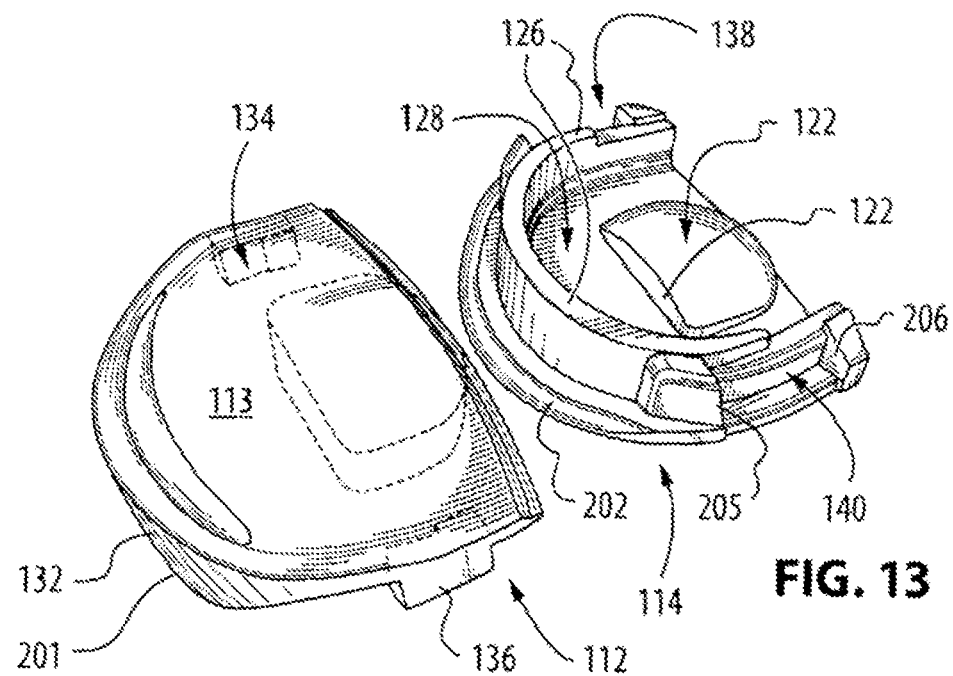
FIG. 13 is a side perspective elevation of the disc of FIG. 12 with the inferior and superior shells separated.

FIG. 13 illustrates the disc 110 in the open state, wherein the superior 112 and inferior 114 shells are separated. In both FIGS. 12 and 13, the nucleus of the disc is not shown. As can be seen in FIGS. 12 and 13, tabs 134 and 136 are provided on the lateral sides of the superior shell 112 and function similarly to the tab structures discussed above. As with the embodiment discussed previously, the inferior shell 114 of disc 110 is provided with a pair of slots 138 and 140, with one slot being provided on each lateral side of the inferior shell 114. As above, the slots 138 and 140 are adapted to receive the tabs 134 and 136, respectively, when the shells 112 and 114 are assembled to form the disc 110. In the embodiment of FIGS. 12 and 13, it can be seen that the slots 138 and 140 are sized so as to have a width that is greater than the width of the associated tabs 134 and 136. As discussed above, such an arrangement serves to allow some degree of translational movement of the tabs 134 and 136 within the associated slot 138 and 140. Such a freedom of movement between the slots and tabs allows the superior and inferior shells 112 and 114 to rotate with respect to each other thereby allowing a degree of axial rotation movement of the spinal segment wherein the disc 110 is implanted. It will be understood that the degree of rotational movement may be tailored by sizing either the slots or tabs. Although a single tab on each side of the disc has been described, it will be understood that any number of tabs may be provided for achieving the same result. Further, in other embodiments, the positions of the tabs and slots may be reversed wherein the tabs are provided on the inferior shell and the slots are provided on the superior shell.

Figure 14:
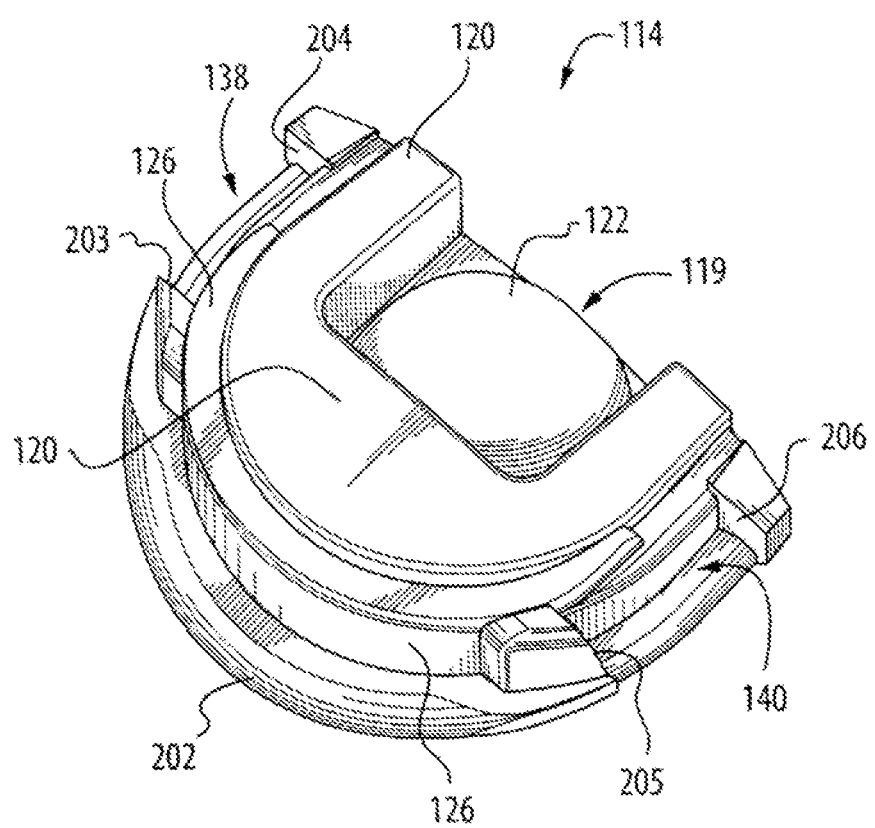
FIG. 14 is a top perspective elevation of the inferior shell of FIG. 12.

FIG. 13 also illustrates the generally "U" shaped well 128 defined by the outer wall 126 of the inferior shell 114. As discussed above, the well 128 accommodates the nucleus (not shown in FIGS. 12 and 13) of the disc 110. FIG. 14 illustrates the inferior shell 114 wherein the nucleus 120 is accommodated within the well 128 shown in FIG. 13.

The inferior shell 114 shown in FIGS. 13 and 14 includes a convex surface or ball 122 that cooperates with a concave surface (not shown in FIGS. 13 and 14) of the superior shell 112 in the same manner as described above.

As described with respect to the previous embodiments, the superior shell 112 is provided with a rim 132 on the anterior end 116 thereof. The rim 132 extends in a direction towards the inferior shell 114 when the disc 110 is in the assembled and implanted state. In one embodiment, as shown in FIGS. 12 to 14, the inferior portion of the inferior shell may be provided with, or extended to form, a lip 202 extending anteriorly and adapted to be positioned under the inferior edge 201 of the rim 132. As will be described further below, the lip 202 would serve as a further hard stop for the disc 110 during a flexion motion.

The slots 138 and 140 of the inferior shell are defined by anterior walls 203, 205 and posterior walls 204, 206, respectively. As discussed above, the slots 138 and 140 and the tabs 134 and 136 are respectively sized so as to allow the tabs to move within the respective slots when the disc 110 is subjected to an axial rotation movement. In such movement, it will be understood that the anterior edge of one of the tabs will abut the anterior wall of its associated slot while, simultaneously, the posterior edge of the other of the tabs will abut the posterior wall of its associated slot. When the disc 110 is rotated in the opposite direction, it will be understood that the opposite edges and walls will be abutting.

Figure 15:
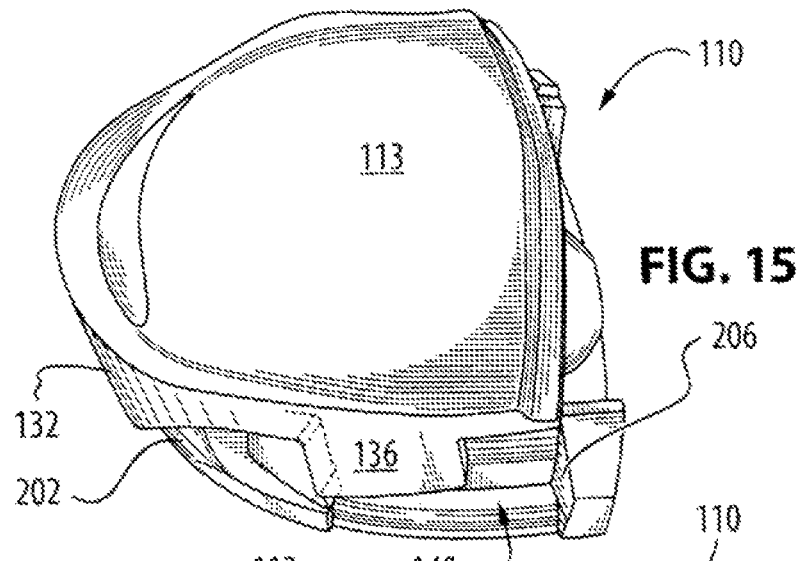
FIG. 15 is a side perspective elevation of the disc of FIG. 12 in a state of flexion.
Figure 16:
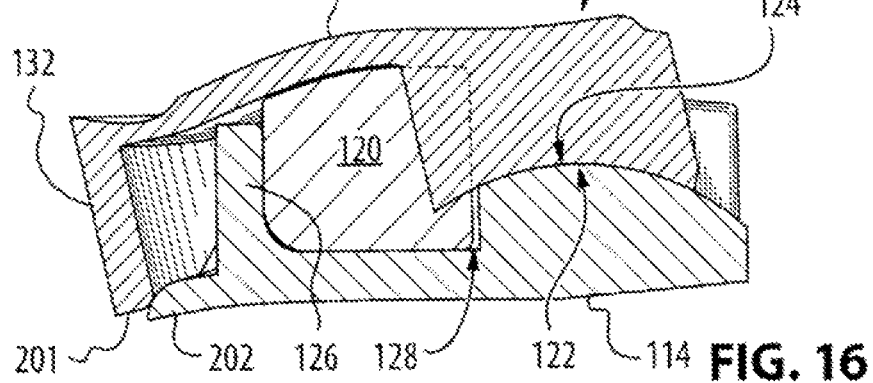
FIG. 16 is a side cross sectional elevation of the disc of FIG. 15.

FIGS. 15 and 16 illustrate the disc 100 during a flexion (i.e. posterior to anterior) motion. As shown and as discussed above, during such motion, the superior and inferior shells articulate over the ball and socket type of connection formed between the convex surface (or ball) 122 of the inferior shell 114 and the concave surface (or socket) 124 of the superior shell 112. It will be understood that such articulation occurs for all translational and rotational movements that occurs between the shells 112 and 114. As shown in FIG. 16, during flexion, the superior shell 112 articulates over the inferior shell 114 thereby resulting in compression of the nucleus 120 between the body of the socket portion 124 and the outer wall 126 of the inferior shell 114. The flexion motion is capable of continuing until the resilient nucleus 120 is no longer capable of being compressed. It will be understood that the compression of the nucleus 120 serves as a gradual or "soft" stop for such flexion motion. However, in order to provide a "hard" stop, the embodiment illustrated in FIGS. 15 and 16 are provided with other features. For example, as discussed above, the inferior shell 114 may be provided with a lip 202 that extends anteriorly underneath the inferior edge 201 of the rim 132 of the superior shell 112. As shown in FIGS. 15 and 16, in such an arrangement, flexion motion of the disc 110 is prevented upon the inferior edge 201 contacting the superior surface of the lip 202. Alternatively or in combination, the anterior walls 203 and 205 of the slots 138 and 140, respectively, may also be sized so as to abut the anterior edges of the tabs 134 and 136, respectively, to serve as a hard stop for flexion movement. This feature is illustrated in FIG. 15 wherein the disc 110 is shown in the full flexion state and wherein the anterior edge of the tab 136 abuts the anterior wall 205 of the slot 140 (it will be understood that the tab 134 similarly abuts the anterior wall 203 of the slot 138).

Figure 17:
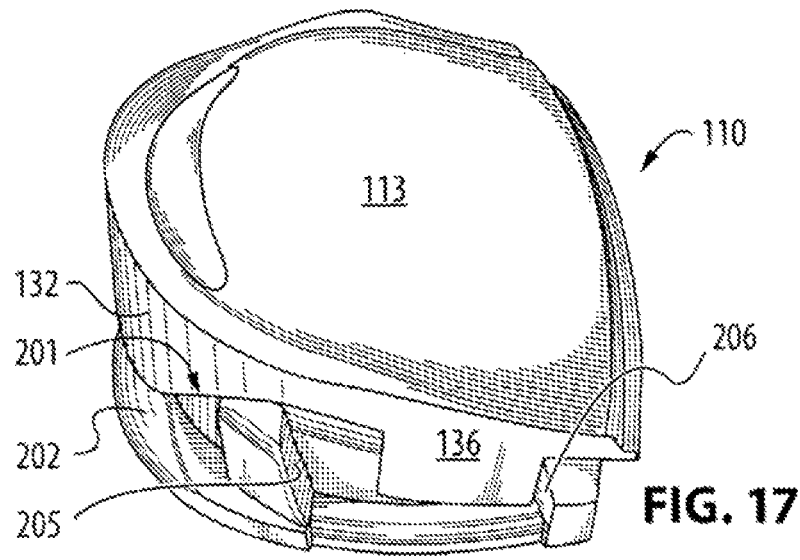
FIG. 17 is a side perspective elevation of the disc of FIG. 12 in a state of extension.
Figure 18:
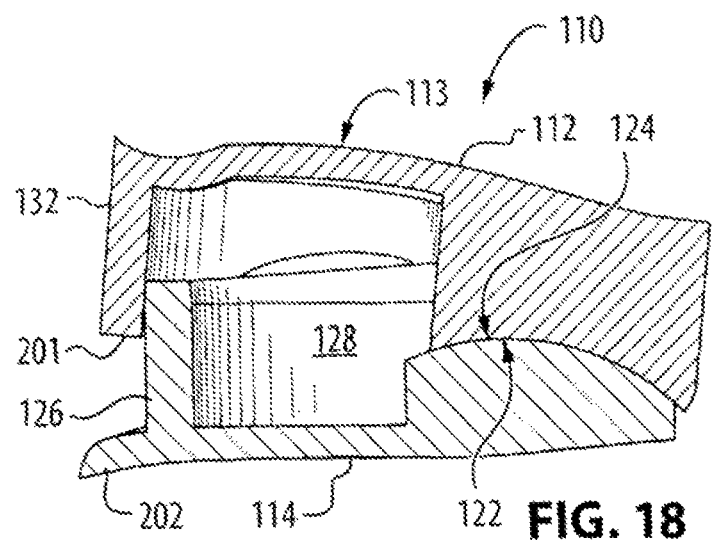
FIG. 18 is a side cross sectional elevation of the disc of FIG. 17.

FIGS. 17 and 18 illustrate the disc 110 of the embodiment in an extension (i.e. anterior to posterior) movement. In FIG. 18, the nucleus 120 has been omitted for clarity thereby illustrating the well 128. As discussed above, the "hard" stop for the extension motion occurs when the posterior surface of the rim 132 contacts the anterior surface of the wall 126. As shown in FIG. 18, such contact occurs generally at the superior edge of the wall 126; however, it will be understood that this will depend upon the degree of clearance provided between the rim 132 and the wall 126. That is, if the separation between the rim 132 and the wall 126 is smaller than that illustrated, the contact region between the two during extension will be positioned inferiorly. FIG. 17 illustrates a further hard stop for the extension motion involving the tabs 134 and 136 and the respective slots 138 and 140. That is, as discussed above with respect to flexion, during extension, the posterior edges of the tabs 134 and 136 are moved towards the posterior walls 204 and 206 of the slots 138 and 140, respectively. Thus, as will be understood, such movement would be prevented from progressing upon the posterior edges of the tabs 134 and 136 contacting the posterior walls 204 and 206 (i.e. a "hard" stop is reached).

FIG. 19 illustrates the disc 110 of the embodiment (but without the nucleus 120) in a lateral (side to side) motion between the superior and inferior shells 112, 114. As shown in FIG. 19, a right to left movement of the superior shell 112, with respect to the inferior shell 114, involves an articulation of the socket 124 over the ball 122. Such movement is continued until the inferior edge 207 of the tab 136 contacts the base 208 of the slot 140 at which point, further lateral movement is prevented. It will also be noted in FIG. 19 that the wall 126 provided on the inferior shell 114 is tapered upwardly. As will be understood, this arrangement will be preferred in order to allow the tab 134 to rise during the right to left movement without contacting the wall 126. The above description has focussed on a right to left movement; however, it will be understood that a similar stop will be encountered during a left to right lateral movement as well. As also illustrated in FIG. 19, during a lateral movement, one side of the disc is compressed and, in the result, any portion of the nucleus (not shown) that may be present in the well 128 or enclosure, would be subjected to compression and thereby offer a "soft" stop for such movement.

It should also be noted that although the above description of the disc 110 has discussed specific movements in single planes, various combinations of movements will be possible with the present invention.

Figure 20:
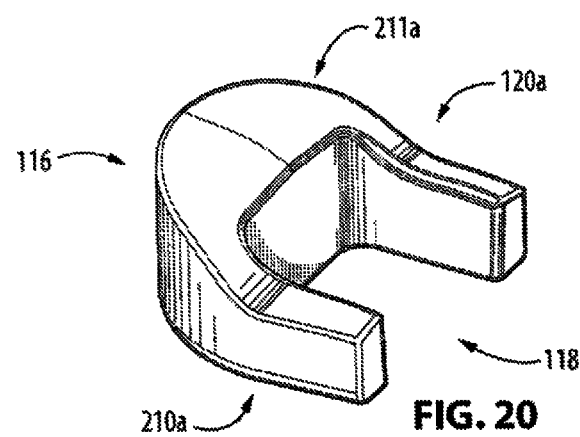
FIGS. 20 and 21 are side elevations of nuclei of the invention.
Figure 21:
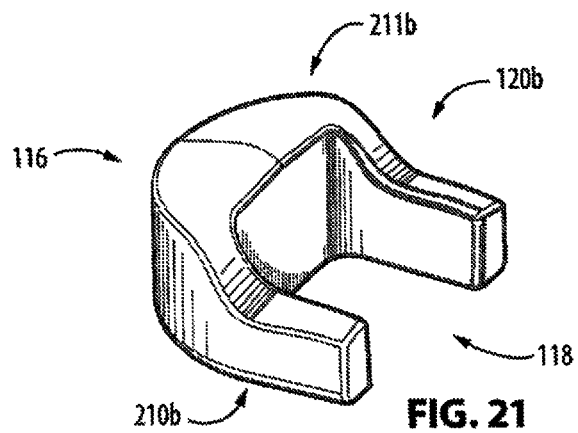

FIGS. 20 and 21 illustrate various alternate embodiments of the nucleus according to one embodiment of the invention. For clarity, the two embodiments of these figures are indicated as 120a and 120b, respectively. In the embodiments shown, the nuclei 120a and 120b are shown as having a generally "U" shaped structure with the arms of the "U" shape extending towards to posterior end 118 of the disc (not shown). Each of the nuclei 120a and 120b have inferior surfaces 210a, 210b and superior surfaces 211a, 211b, respectively. As shown, the inferior surfaces 210a and 210b are generally planar and are adapted to be accommodated within the well of the inferior shell of the disc (as discussed above). In the embodiments shown in FIGS. 20 and 21, the anterior (i.e. in the direction of 116) portion of the nuclei 120a, 120b are provided with thickened sections whereby the anterior ends of the superior surfaces 211a, 211b of the nuclei rise above the posterior ends. In FIG. 20, the superior surface 211a is further provided with an inclined shape. With the structure of the nuclei shown in FIGS. 20 and 21, it will be understood that a greater separation force will be offered by the nuclei to space apart the superior shell from the inferior shell. Further, by concentrating such separation force on the anterior end (116) of the disc, the nuclei of FIGS. 20 and 21 cause the spinal segment in which the disc is implanted into the neutral position when the individual is upright. That is, the increased separating force applied to the anterior end of the disc will allow a degree of compression (such as to accommodate the weight of the individual's head) and still result in the segment to assume the neutral position. It will be understood that this feature may be of importance primarily for discs implanted into cervical spinal segments or where accommodation is desired to account for compression of the nucleus due to overlying weight. The specific situations where such an accommodation is required will be apparent to persons skilled in the art.

SUMMARY OF FEATURES OF THE INVENTION

The artificial discs (e.g. 10, 10a etc.) of the present invention includes various features, which will now be summarised. Firstly, in one aspect, the disc includes various structural components to accommodate individual and coupled movements such as axial rotation, lateral bending, and flexion/extension. In the result, the prosthetic disc of the invention generally reproduces neutral zone and elastic zone movements associated with a natural intact disc. Further, the invention allows for unconstrained and/or partially constrained coupled movements by means of engineered endpoints that prevent excessive or non-physiological movement. The fully constrained stop mechanisms (i.e. the "hard stops") ensure that movement is, for example, not extended past the elastic zone.

In another embodiment, the disc of the invention may be generally wedge shaped in the sagittal plane so as to integrate with and promote a lordotic spine configuration. Such an implant may be used in cases where spinal re-alignment is sought. For example, the disc may have a larger height at the anterior end as compared to the height of the posterior end to provide the aforementioned wedge shape. Similarly, such a difference in height may also be provided between the lateral sides of the disc, that is in the coronal plane. This type of configuration may be used, for example, to correct a malalignment such as scoliosis.

The generally spherically curved external surfaces of the shells provide the disc of the invention with an ovoid curvature in the coronal plane. This structure maximises disc to bone surface area and thereby promotes bony in-growth. Such structure also maximises prosthetic occupation of the disc space while stabilizing the disc against bone after implantation.

As discussed above, the ball and socket-like joint formed between the superior and inferior shells allows for complex relative motions there-between. The "ball" portion can be provided with a variety of geometries (e.g. radii of curvature) and in a variety of positions over the inferior shell to create different axes of rotation based on the need. It will be understood that a concomitant positioning of the socket portion of the superior shell will also be made in order to provide the ball and socket joint arrangement described above. In other embodiments, the ball portion may be movable in one or more planes within a constrained space so as to allow the instantaneous axis of rotation to be dynamically variable and allow for greater variability in the range of motion provided by the disc of the invention.

Various "hard stops" are provided to inhibit excess lateral, rotational and extension movement between the shells.

The external surfaces of the superior and inferior shells may be curved or spherical (i.e. ovoid, elliptical) or straight (i.e. squared) for insertion into bi-concave or rectangular discectomy sites at any area of the spine. The external surfaces may optionally be provided with anchoring ribs or keels for securing the disc to adjacent bone structures or to other artificial spinal structures.

In one embodiment, the superior shell may be larger in diameter, as taken in the sagittal plane (i.e. the anterior-posterior direction), than the inferior shell so as to better approximate the "normal" condition.

In one embodiment, the outer surface of the disc of the invention can be provided with one or more markings or physical features to render same opaque under radiography. As will be understood, such features would aid in post-operatively verifying the alignment and/or positioning of the implant.

The footprint of the disc is preferably maximised in both the coronal and sagittal planes to help eliminate subsidence. As will be understood, the size of the discs of the invention will vary to accommodate various sizes of discs in the normal spine.

Although the invention has been described with reference to certain specific embodiments, various modifications thereof will be apparent to those skilled in the art without departing from the purpose and scope of the invention as outlined herein. The entire disclosures of all references recited above are incorporated herein by reference.

We claim:

1. An artificial intervertebral disc for implantation between adjacent superior and inferior vertebrae of a spine, the disc comprising:
    a superior shell, an inferior shell, and a resilient nucleus, wherein the nucleus is a unitary and generally "U" shaped body;
    the superior and inferior shells being movable with respect to each other;
    the inferior shell having a superior surface, the superior surface including an integral convex portion and a generally "U" shaped well, the convex portion being posteriorly positioned on the superior surface of the inferior shell;
    the superior shell having an inferior surface opposing the superior surface of said inferior shell, the inferior surface including an integral concave portion and a generally "U" shaped recess, the concave portion being posteriorly positioned on said inferior surface, wherein the concave portion is opposite to said convex portion and the recess is opposite the well when the inferior shell and superior shell are aligned;
    the well and recess combining to form an enclosure to contain said nucleus;
    the convex portion of the inferior shell and concave portion of the superior shell being in articulating cooperation to form a ball and socket joint
    wherein said superior shell includes a first wall and said inferior shell includes a second wall, said first and second walls being positioned at an anterior end of the disc, at least a portion of said walls being overlapped wherein said first wall extends downward and said second wall extends upward and is positioned posteriorly of said first wall; and,
    wherein said inferior shell includes an anteriorly extending lip for limiting anterior movement of said first wall.

2. The artificial disc of claim 1 wherein said nucleus applies a biasing force to elastically separate the inferior and superior shells.

3. The artificial disc of claim 1 wherein said nucleus is provided at least in an anterior section of the disc.

4. The artificial disc of claim 1 further comprising one or more motion regulating means to limit or prevent relative movement between the superior and inferior shells in one or more planes.

5. The artificial disc of claim 1 wherein one of the superior or inferior shells includes one or more inferiorly depending tabs on lateral sides thereof and the other of the superior or inferior shells includes slots for receiving said tabs.

6. The artificial disc of claim 5 wherein said tabs are provided on the superior shell and said slots are provided on the inferior shell.

7. The artificial disc of claim 1 wherein said second wall prevents posterior movement of said first wall whereby extension motion of the disc is limited.

* * * * *